United States Patent [19]
Matthews

[11] Patent Number: 6,149,273
[45] Date of Patent: Nov. 21, 2000

[54] OPHTHALMOSCOPE AND IMAGE DETECTION MEANS

[75] Inventor: James Robert Arnold Matthews, Bracknell, United Kingdom

[73] Assignee: Keeler Limited, Windsor, United Kingdom

[21] Appl. No.: 09/393,430

[22] Filed: Sep. 10, 1999

Related U.S. Application Data

[60] Provisional application No. 60/108,623, Nov. 16, 1998.

[30] Foreign Application Priority Data

Sep. 11, 1998 [GB] United Kingdom .................... 9819714

[51] Int. Cl.$^7$ ........................................................ A61B 3/10
[52] U.S. Cl. ............................................................ 351/221
[58] Field of Search .................................. 351/200, 205, 351/206, 209, 210, 218, 221

[56] References Cited

U.S. PATENT DOCUMENTS 4,856,891  8/1989  Pflibsen ..................................... 351/210
5,673,097  9/1997  Heacock .................................... 351/221

*Primary Examiner*—George Manuel
*Attorney, Agent, or Firm*—Lee, Mann, Smith, McWilliams, Sweeney & Ohlson

[57] ABSTRACT

An indirect ophthalmoscope is equipped with a camera (14) to enable the view seen by the user of the ophthalmoscope to be displayed. Light is reflected into the camera by a reflector such as a prism (16) which is preferably substantially co-planar with the ophthalmoscope's optical elements (through which the user sees an eye under examination). The prism (16) and camera (14) are centrally mounted on the ophthalmoscope through mounting means, such as a frame, which has adjustment means for adjusting the positions of the prism and camera relative to the ophthalmoscope so as to alter the position of the field of view of the camera relative to the ophthalmoscope's optical elements. The adjustment means help to ensure that the field of view of the camera, and hence the displayed image, corresponds to the view seen by the user of the ophthalmoscope. The camera, prism and frame may form part of an attachment which may be retrofitted to an existing ophthalmoscope.

14 Claims, 3 Drawing Sheets

OPHTHALMOSCOPE AND IMAGE DETECTION MEANS

RELATED APPLICATIONS

This Application claims the benefit of U.S. provisional Patent Application No. 60/108,623 filed Nov. 16, 1998.

FIELD OF THE INVENTION

This invention relates to ophthalmoscopes, in particular indirect ophthalmoscopes, and to image detection devices for use therewith.

BACKGROUND TO THE INVENTION

It is known to fit an indirect ophthalmoscope with a camera for detecting an image of the retina being observed, through a condensing lens, by the user. Such ophthalmoscopes are often used in the instruction of students or to inform patients or their relatives, since the image of the retina being observed by an ophthalmologist using the instrument can be displayed on a separate video display unit in real time. The image can also be recorded for subsequent analysis. It is also envisaged that, with the advent of improved telecommunications systems, a non-specialist could use the ophthalmoscope to provide an image which is transmitted to an specialist at a remote location so that the specialist can examine the eye without visiting the patient.

Typically, an indirect ophthalmoscope is a binocular device having viewing optics which have two central mirrors arranged to direct respective images to the left and right eye of the person using the ophthalmoscope. Conventionally, the camera detects an image reflected from an angled half-silvered mirror disposed immediately in front of the two mirrors. It is common for ophthalmoscopes to include head gear to enable them to be used on the user's heads.

Conventionally, the field of view of the camera, i.e. the area imaged by the camera with the aid of the mirror, is fixed relative to the ophthalmoscope. In practice, however, a user may adjust the attitude of the ophthalmoscope relative to his/her head so that the image seen through the viewing optics does not lie wholly within the field of view of the camera.

This can lead to some confusion since the image displayed or recorded using the camera will not then be the same as that seen by the user.

A known type of camera attachment for an ophthalmoscope, produced by Litechnica, includes a facility for adjusting the field of view of the camera, but this attachment makes the instrument lopsided. In addition, light from the image to be detected is reflected into the camera by means of a mirror which is situated on the opposite side of the viewing optics of the ophthalmoscope. Consequently, the image detected by the camera is not congruent with that seen through the viewing optic.

SUMMARY OF THE INVENTION

According to a first aspect of the invention, there is provided an ophthalmoscope for examining an eye, the ophthalmoscope comprising an arrangement of optical elements for directing light from an eye under examination to a user, and mounting means for image detecting means for detecting an image in the field of view of the image detecting means, wherein the mounting means includes adjustment means for altering the position of the field of view of the image detecting means relative to said arrangement of optical elements, and is so arranged as to retain the image detecting means in a substantially central position on the ophthalmoscope.

The adjustment means can be used to ensure that the field of view of the image detecting means corresponds to the view seen by the user of the ophthalmoscope. For example, if the image detecting means is connected to a display, the adjustment means can be operated by a third party who can view the display, whilst the user describes the image seen through the viewing optics, until the field of view does correspond to the image seen through the viewing optics.

Since the mounting means enables the image detecting means to be centrally positioned on the ophthalmoscope, the invention enables a camera to be mounted on the ophthalmoscope without adversely affecting the lateral weight distribution of the instrument.

Preferably, the image detecting means comprises a camera and reflecting means for directing light from said field of view into the camera, the adjustment means being operable to alter the position of at least one, preferably both, the camera and the reflecting means relative to the viewing optics.

Preferably, the adjustment means is operable to pivot the camera and reflecting means about an axis which, with the ophthalmoscope in its normally intended attitude of use, is substantially horizontal.

Preferably, the mounting means comprises a rigid frame on which the camera and reflecting means are mounted. In this case, the adjustment means preferably comprises a pivot through which the frame is mounted on the housing, and an abutment for engaging the frame to limit the extent of pivotal movement of the latter in one sense, the adjustment means also including biasing means for biasing the frame against the abutment.

Adjustment of the abutment in one direction urges the frame in one sense against the action of the biasing means, whilst adjustment in the other direction allows the biasing means to pivot the frame in the opposite sense.

Preferably, the abutment means comprises a screw.

Preferably, the image detecting means is so positioned that light forming the image detected by the detecting means is incident on the latter at apposition which is horizontally or vertically spaced from the path of light from the eye under examination to said arrangement of optical elements.

This arrangement has the advantage that the image detecting means does not block any light travelling from the eye under observation to the viewing optics, and therefore does not reduce the intensity of image seen through the viewing optics.

Where the ophthalmoscope is a binocular instrument, the arrangement of optical elements having two spaced apart mirrors via which the arrangement receives the light from the eye under examination, the image detecting means preferably has a portion for receiving the light forming the image to be detected, and from which the mirrors are or can be laterally spaced in opposite directions.

Conveniently, the portion of the detecting means is positioned in a position forward of the arrangement of optical elements.

Preferably, the portion comprises said reflecting means. In this case, the camera of the image detecting means is preferably situated above the reflecting means. Consequently, the camera and reflecting means are centrally positioned, and have little or no effect on the lateral weight distribution of the ophthalmoscope.

Preferably, the reflecting means and the optical elements of the ophthalmoscope are substantially co-planar. This feature avoids the problem of the images displayed on the monitor and seen by the user only being congruent for a certain position of the condenser lens being used in conjunction with the ophthalmoscope.

Preferably, the reflecting means is arranged to reflect the image of an eye under examination at least twice before the image is received by the camera, so as to eliminate any mirror inversion of the image seen by the camera.

To that end, the reflecting means preferably comprises a pentagonal prism, for example a penta prism.

A prism is particularly advantageous because it is a very efficient reflector of light, and because the relative position of the two surfaces from which the reflections occur is constant.

The invention also lies in image detection means for an ophthalmoscope according to the first aspect of the invention, the image detecting means comprising a frame, reflecting means mounted on the frame, means on the frame for receiving a camera in a position opposed to the reflecting means, and mounting means for mounting the frame on the front of an ophthalmoscope, the mounting means having adjustment means for adjusting the position of the frame, when so mounted, relative to the ophthalmoscope.

According to a further aspect of the invention, there is provided an ophthalmoscope having an arrangement of optical elements via which, in use, an eye under examination is viewed, image detecting means for detecting an image in its field of view and adjustment means for altering the position of said field of view relative to the arrangement of optical elements.

BRIEF DESCRIPTION OF THE DRAWINGS

The invention will now be described, by way of example only, with reference to the accompanying drawings, in which.

DETAILED DESCRIPTION

Figure 1:
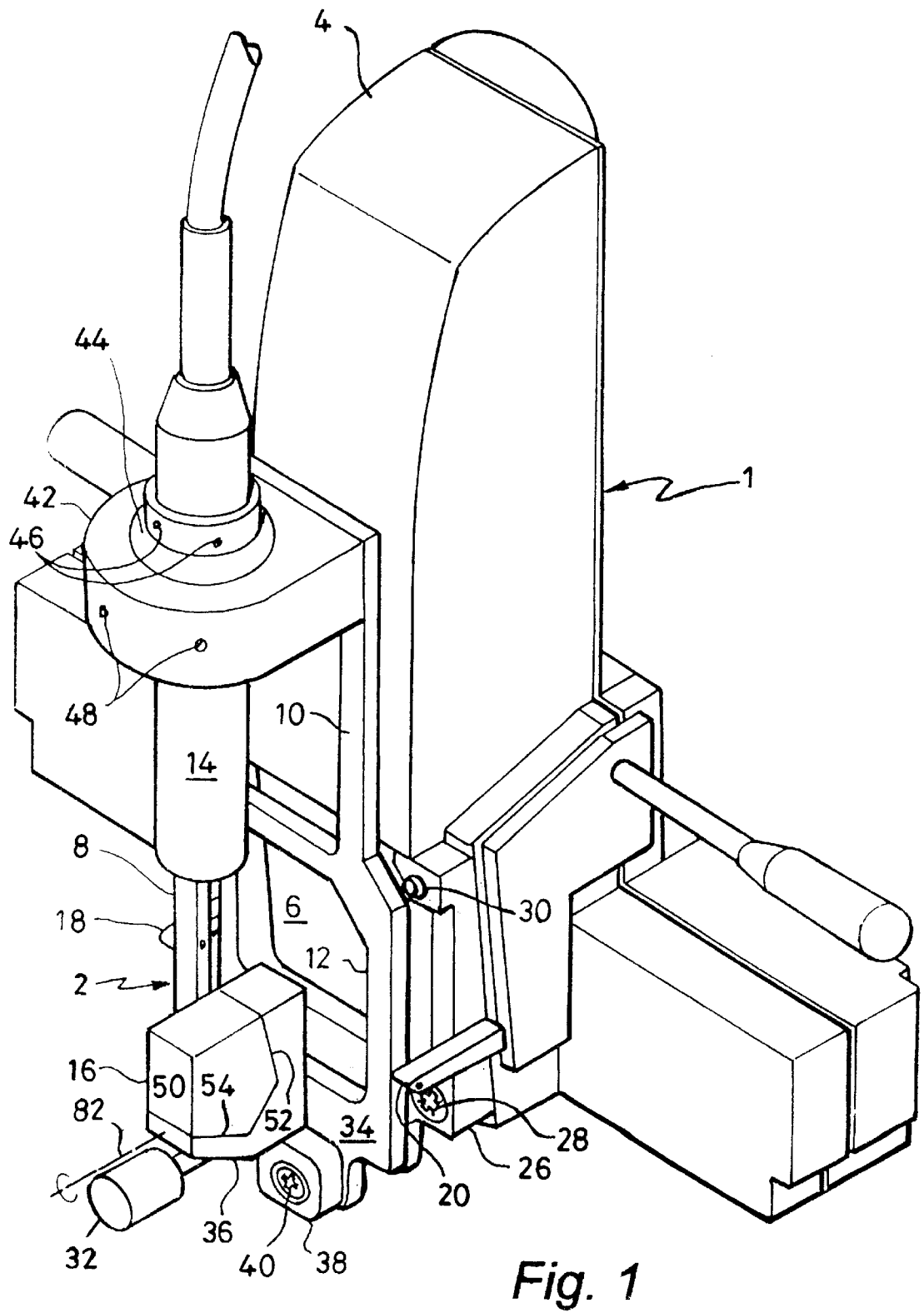
FIG. 1 is a perspective view of an ophthalmoscope and attachment according to the invention.

With reference to FIG. 1, reference numeral 1 generally denotes an indirect ophthalmoscope which, in this example, is of the type currently supplied by the Applicants under the Trade Mark KEELER VANTAGE. This ophthalmoscope can be retrofitted with an attachment, generally referenced 2, to provide an ophthalmoscope in accordance with the invention.

The ophthalmoscope 1 is provided with a headset (not shown) to enable the ophthalmoscope to be mounted on the head of a user, and has a housing 4 for a light source, and illuminating optics .

Figure 2:
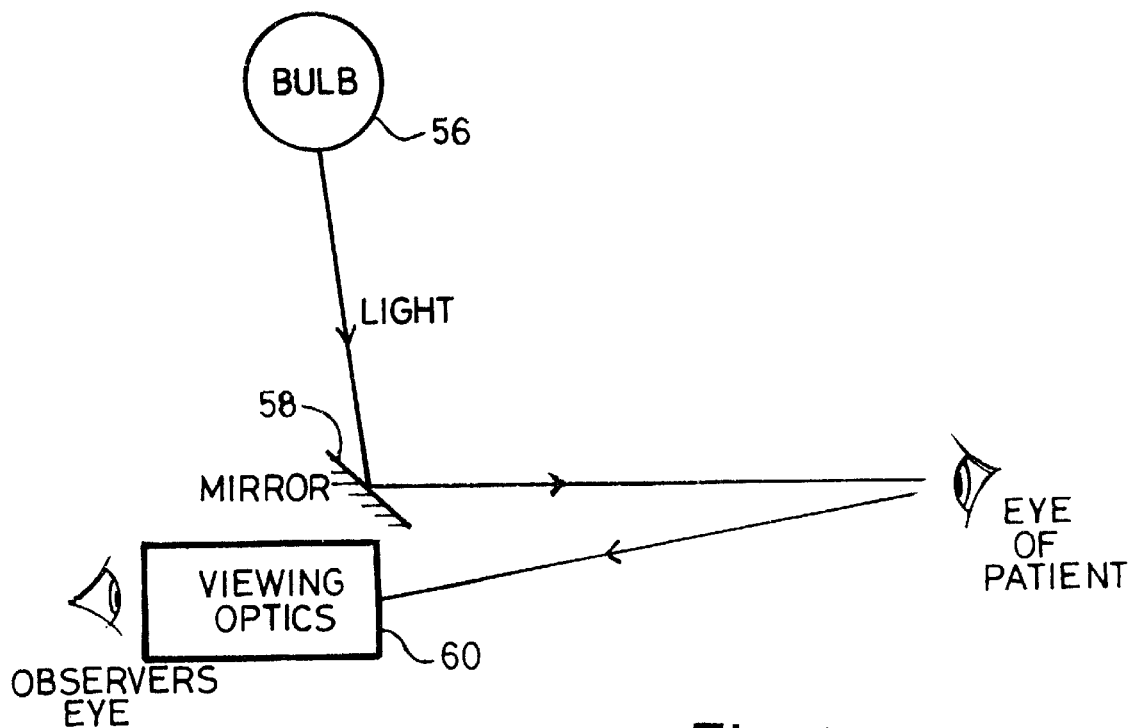
FIG. 2 is a schematic side view of the illuminating optics of the ophthalmoscope.

With reference to FIG. 2, the illuminating optics comprise a light bulb 56, light from which is reflected from an angled planar mirror 58 in the housing 10, to an eye to be examined (indicated as the "eye of patient"). Light from the patient's eye travels back to the ophthalmoscope to enter the viewing optics of the latter. Reference numeral 60 denotes the viewing optics, some components of which are shown in more detail in FIG. 4, and are described below.

The front of the housing 4 includes a window 6 through which Light from the illuminating optics exits the housing 4, and light from the eye under examination reaches two spaced apart light receiving elements of the binocular viewing optics.

In use, the illuminating light beam is reflected from the planar mirror 58 and passes through a hand-held lens (usually plus 20D) before reaching the patient's eye. The user of the ophthalmoscope views the illuminated eye through the binocular viewing optics. The illuminating beam path does not coincide with the path of light reflected from the eye into the viewing optics since the re is vertical separation and therefore an acute angle between those two paths.

The viewing optics 60 include two light receiving elements, each comprising a respective one of two mirrors 62 and 64 mounted on triangular mirror blocks 66 and 68 which are, in turn, supported on a platform 70. The platform 70 also supports two further, triangular mirror blocks 72 and 74 positioned one on either side of the mirrors 62 and 64. The further blocks carry corresponding further mirrors 76, 78 (also part of the viewing optics) and have apertures (eg 80) to allow light reflected from the mirrors 62 and 64 to travel to the reflective surfaces of mirrors 76 and 78 from which the light is reflected into eye pieces (not shown) forming part of the viewing optics and situated behind the platform 70.

All the mirror blocks 66, 68, 72 and 74 are all slideably mounted on the platform 70, and the ophthalmoscope includes mechanisms, not shown, for varying the separation between the blocks 66 and 68 (to adjust the stereopsis of the ophthalmoscope) and between the blocks 72 and 74 to enable the ophthalmoscope to accommodate a range of different interpupillary distances of its users.

The attachment 2 comprises a frame 8 having upper and lower generally rectangular portions, respectively referenced 10 and 12. The upper portion carries a camera 14, whilst a penta prism 16 is mounted at the bottom of the lower portion 12.

The frame 8 is pivotally connect ed to a pair of opposed arms 18 and 20 which are in turn attached to a rectangular mounting frame 26 adapted to be attached to the front of the ophthalmoscope 1. The top of the mounting frame 26 has two spaced apart tongues (not visible in FIG. 1) which slide up under the front vents of the ophthalmoscope 1. The bottom portion of the frame 26 has two apertures, one on either side, for receiving respective screws, one of which is shown at 28. The screws extend into screw-threaded bores in the front of the ophthalmoscope 1 so that the frame 26 is securely located on the latter.

As can be seen from FIG. 1, both the frame 26 and the portion 12 have central openings in registry with the window 6.

Two compression springs, one of which is shown at 30, are situated towards the top of the portion 12 and the mounting frame 26, and act between the frame a and the mounting frame 26 to bias the top of the frame 8 away from the ophthalmoscope 1, and hence the portion of the frame 8 below the pivotable arms 18 and 20, towards the mounting frame 26. The extent of movement towards the mounting frame 26 is limited by an abutment which comprises an adjustment screw 32. The screw 32 extends through a screw-threaded through bore in a cross-member 34 at the bottom of the portion 12 to bear against the mounting frame 26. The screw 32 is thus urged against the mounting frame 26 by the springs 30, and the rotation of the screw 32 will cause the frame 8 to pivot around the pivotal connections at the arms 18 and 20, and hence about a horizontal axis passing through those connections.

The prism 16 is securely held within a bracket 36 from which an apertured lug 38 extends. The lug 38 is, in turn, screwed onto the bottom of the portion 12 using a screw 40. The screw shaft is of a smaller aperture than the aperture, and a pin (not shown) extends from the bracket 36 into the bottom portion 12. This mode of attachment of the prism 16 enables the position of the latter to be adjusted by loosening the screw 40 and rotating the bracket 36 about the axis of the pin before tightening the latter to fix the orientation of the prism 16. The axis about which the bracket can rotate is indicated at 82 in FIG. 1.

Figure 3:
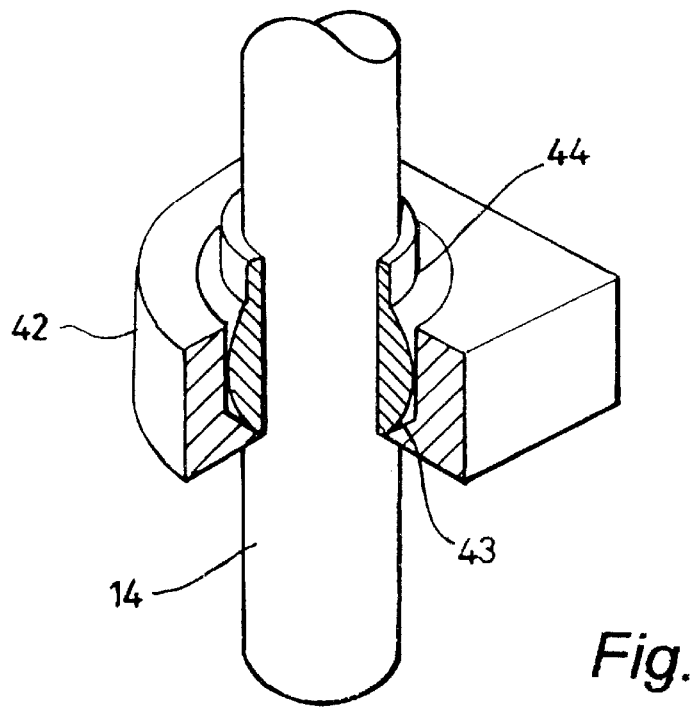
FIG. 3 is a more detailed, cut-away view of part of the ophthalmoscope.

With reference to FIGS. 1 and 3, a further bracket 42 extends forwardly from the top of the portion 10 and includes a vertical passage 43 having a cylindrical upper portion and a frustoconical Lower portion. The passage 43 accommodates a ball sleeve 44 through which the camera 14 extends and is securely fixed thereto by means of two grub screws 46. The ball sleeve 44 can move within the passage in the bracket 42 to allow the orientation of the camera 14 to be adjusted. Once a suitable orientation has been selected, the position of the ball sleeve 44 relative to the bracket 42 is fixed by means of a pair of radial grub screws 48 which have pointed ends for engaging the exterior of the ball sleeve 44 to hold the latter in position.

A compression spring and ball (not shown) act between the ball sleeve 44 and the passage 43 to hold the sleeve captive in the passage even when the screws 48 are removed.

Figure 4:
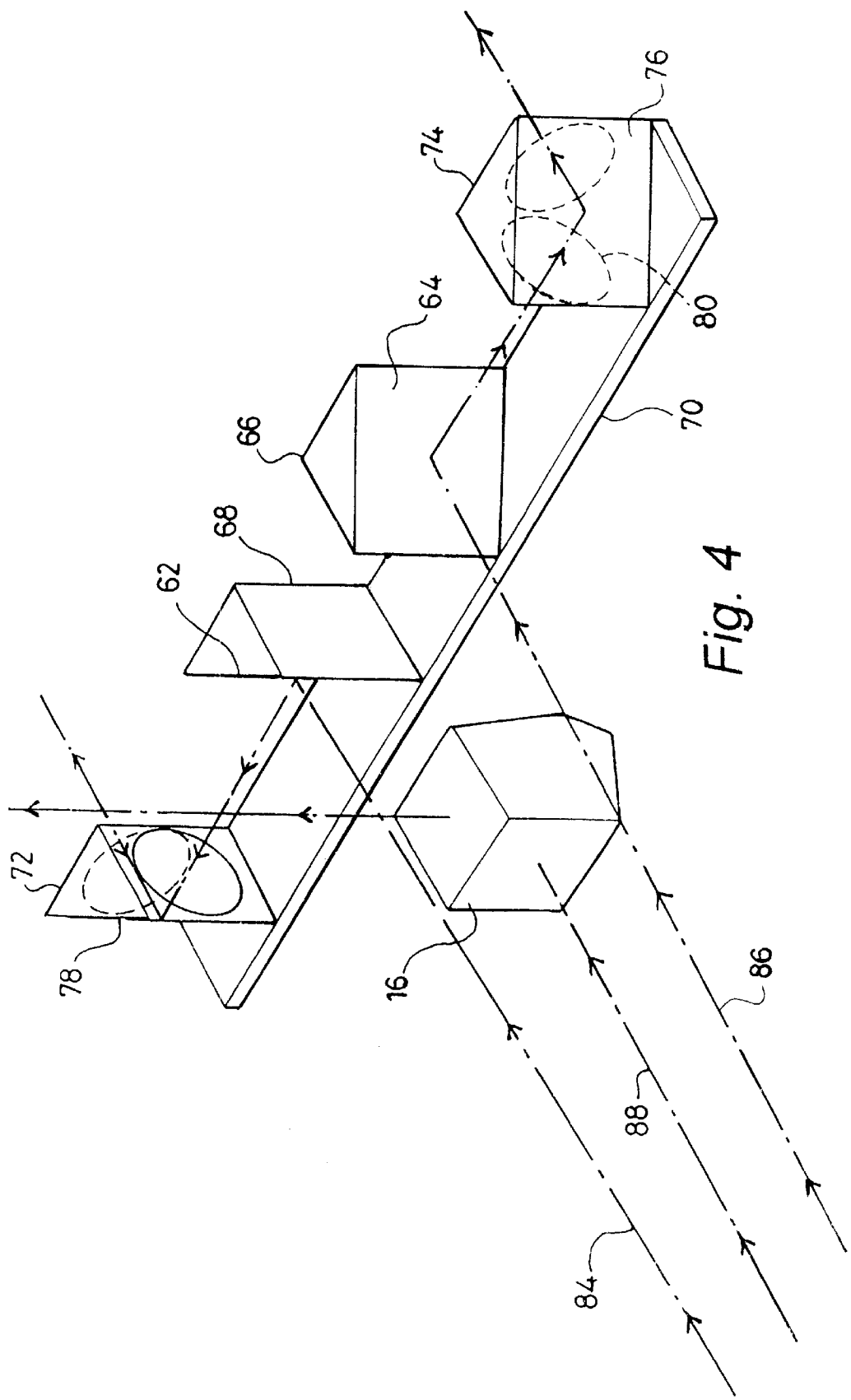
FIG. 4 is a simplified diagram illustrating the relative positions of parts of the viewing optics and image capture means of the ophthalmoscope.

As can be seen from FIGS. 1 and 4, the prism 16 is centrally located on the bottom portion 12 of the frame 8 and is substantially co-planar with the mirrors 62 and 64. When the separation between the mirrors 62 and 64 is at a minimum, the prism holder 36 does partially occlude the two mirrors 62 and 64. However, when the stereopsis is set at a maximum, so that the separation between the mirrors 62 and 64 is also at a maximum, the mirrors 62 and 64 are laterally spaced, in their entireties, in opposite directions from the prism 16 and the holder 36. Consequently, when the ophthalmoscope 1 is viewed from the front, the prism 16 would appear between the two mirrors. As a result, the user of the ophthalmoscope looks past either side of the prism 16.

This can be seen from FIG. 4, in which the separation between the mirrors 62 and 64 is such that light travelling from the eye under examination to the viewing optics travels along paths, for example paths 84 and 86 which straddle the prism 16, whilst the camera 14 receives light, reflected by the prism 16, which has travelled along paths, for example path 88, which are laterally spaced from the mirrors 62 and 64, and hence from the path of light thereto.

Light from an eye under examination enters the prism 16 through a front face 50 and travels to a rear upper-angled face 52 which reflects the light down and forward onto a further angled face 54. The face 54, in turn, reflects light from the face 52 directly up into the camera 14. Consequently, the image of the eye under examination is reflected firstly by the face 52 and then by the face 54 before entering the camera 14. As a result of this double reflection, the image entering the camera 14 is not inverted relative to the view seen through the viewing optics of the ophthalmoscope 1.

In this example,.the prism is sold under the Trade Mark MELLES GRIOT and is identified by the reference 01PPA003. The video camera is identified by the Trade Mark "TELI" and produced by Tokyo Electronic Industry Co. Limited. The present example has a product number CS6100, and uses a PML 300-30 mms focal length lens.

It has been found, in practice, that not all users of the ophthalmoscope look straight into the eyepieces of the viewing optics. For example, a wearer of half-moon spectacles, may tilt his/her head forwards relative to the ophthalmoscope so as to view the eye under examination (through the viewing optics) over the tops of the spectacles. Consequently, the image detected by the camera 14 may not correspond with that being viewed by the user. However, this difference can be eliminated by using the screw 32 to pivot the frame 8 about the pivotal connection to the arms 18 and 20 until the rays of light which the prism 16 reflects up into the camera 14 are substantially co-planar with those received by the viewing optics. Before the ophthalmoscope is first used with the attachment 2, the attachment 2 is set up by locking the prism 16 and camera 14 in a suitable relative position. This can be achieved with, for example, a suitable jig.

The ophthalmoscope described above is one example of an embodiment of the invention, and various alterations or modifications may be made without departing from the scope of the invention as defined by the claims. Thus, for example, the prism 16 may be replaced by an alternative type of reflecting means, for example a mirror. In such a case, the camera will receive a laterally inverted image, which may be displayed on a monitor or may be electronically re-inverted by image processing circuitry connected between the camera and the monitor.

Furthermore, instead of the frames 8 and 26, the ophthalmoscope may have an alternative type of mount, for example formations which attach the camera and reflector directly to the ophthalmoscope, which enable the position of the camera and reflector to be altered and which therefore also enable the adjustment of the field of view of the camera and reflector.

What is claimed is:

1. An ophthalmoscope for examining an eye, the ophthalmoscope comprising an arrangement of optical elements for directing light from an eye under examination to a user, and a mount for receiving image detecting apparatus for detecting an image in the field of view of the image detecting apparatus, wherein the mount is adjustable to enable the position of the field of view of the image detecting device relative to said arrangement of optical elements to be altered, and is so arranged as to retain the image detection device at a substantially central position on the ophthalmoscope.

2. An ophthalmoscope according to claim 1, in which the mount has formations for receiving image detecting apparatus comprising a camera and reflector for directing light from said field of view into the camera, the adjustment means being operable to alter the position of at least one of the camera and the reflector relative to the viewing optics.

3. An ophthalmoscope according to claim 2, in which said adjustment of the mount adjusts the positions of both the camera and the reflector.

4. An ophthalmoscope according to claim 3, in which the mount enables the camera and reflector to pivot about an axis which, with the ophthalmoscope in a normally intended attitude of use, is substantially horizontal.

5. An ophthalmoscope according to claim 4, in which the mount comprises a rigid frame on which the camera and reflector are mounted, the mount including a pivot through which the frame is mounted on the ophthalmoscope and an abutment for engaging the frame to limit the extent of pivotal movement of the latter in one direction, the mount also including a biasing member for biasing the frame against the abutment.

6. An ophthalmoscope according to claim 5, in which the abutment means comprises a screw.

7. Image detecting apparatus for an ophthalmoscope according to claim 1, the image detecting apparatus comprising a frame, a reflector mounted on the frame, means on the frame for receiving a camera in a position opposed to the reflector, and a mount for mounting the frame on the front of an ophthalmoscope, the mount being adjustable to permit the position of the frame, when so mounted, relative to the ophthalmoscope to be adjusted, thereby to alter the field of view of the image detecting apparatus relative to the ophthalmoscope.

8. An ophthalmoscope having a plurality of optical elements via which, in use, an eye under examination is viewed and an image detecting apparatus for detecting an image in its field of view and wherein the ophthalmoscope includes an adjustable mount for altering the position of said field of view relative to the arrangement of optical elements, and wherein the image detecting apparatus is substantially centrally positioned on the ophthalmoscope.

9. An ophthalmoscope according to claim 8, wherein the ophthalmoscope is a binocular instrument, the plurality of optical elements including two spaced apart mirrors via which the ophthalmoscope receives the light From an eye under examination, and wherein the image detecting apparatus has a portion for receiving the light forming the image to be detected, and from which the mirrors are or can be laterally spaced in opposite directions.

10. An ophthalmoscope according to claim 9, in which the portion of the image detecting means is positioned forward of the arrangement of optical elements.

11. An ophthalmoscope according to claim 8, in which the portion comprises a reflector and a camera is situated above the reflector.

12. An ophthalmoscope according to claim 11, in which the reflector is arranged to reflect the image of an eye under examination at least twice before the image is received by the camera, so as to eliminate any mirror inversion of the image detected by the camera.

13. An ophthalmoscope according to claim 12, in which the reflector comprises a pentagonal prism.

14. An ophthalmoscope according to claim 8, in which the image detecting apparatus comprises a camera and reflector for reflecting light from the field of view up into the camera, the reflector being substantially co-planar with the optical elements.

* * * * *